United States Patent [19]

Neuss et al.

[11] 4,174,772
[45] Nov. 20, 1979

[54] APPARATUS AND METHOD FOR COORDINATING CHROMATOGRAPHIC SEPARATION (HPLC) WITH UV/VIS ABSORBENCY VALUES AND WITH BIOAUTOGRAPH TEST RESULTS

[75] Inventors: Norbert Neuss, Indianapolis; Roger D. Miller, Mooresville, both of Ind.

[73] Assignee: Eli Lilly and Company, Indianapolis, Ind.

[21] Appl. No.: 865,278

[22] Filed: Dec. 28, 1977

[51] Int. Cl.² ............................................... C12K 1/04
[52] U.S. Cl. .................................. 435/32; 210/198 C; 422/70; 435/291
[58] Field of Search ........ 195/103.5 M, 127, 103.5 K; 210/198 C

[56] References Cited

U.S. PATENT DOCUMENTS

| | | | |
|---|---|---|---|
| 3,700,562 | 10/1972 | Morgenstern et al. | 195/127 X |
| 3,902,971 | 9/1975 | Fletcher et al. | 195/127 X |
| 4,013,418 | 3/1977 | Plakas | 195/127 X |

Primary Examiner—Raymond N. Jones
Assistant Examiner—Robert J. Warden
Attorney, Agent, or Firm—Houston L. Swenson; Arthur R. Whale

[57] ABSTRACT

An apparatus is described which is adaptable for use in coordinating UV/VIS absorbency values of a chromatography eluate containing antimicrobial constituents with bioautograph test results. Such an apparatus is comprised of a UV/VIS spectrophotometer equipped with a continuous recording monitor, a pair of parallel metering valves, a stream splitter, a rotatable drum adapted to hold a piece of absorbent material and means to rotate said drum. The method involves the use of such an apparatus in combination with the bioautograph test to coordinate said absorbency valves with the test results from a plurality of bioautograph test organisms.

7 Claims, 5 Drawing Figures

APPARATUS AND METHOD FOR COORDINATING CHROMATOGRAPHIC SEPARATION (HPLC) WITH UV/VIS ABSORBENCY VALUES AND WITH BIOAUTOGRAPH TEST RESULTS

BACKGROUND OF THE INVENTION

1. Field of the Invention

This invention relates to an apparatus for coordinating UV/VIS spectrophotometer absorbency values of a chromatography eluate stream containing antimicrobial constituents with bioautograph test results against a plurality of test organisms. Specifically, the instant invention provides an apparatus to split a chromatography eluate stream into a plurality of smaller streams of essentially equivalent volumes which are absorbed on absorbent material and then evaluated individually against a specific test organism in a bioautograph test to simultaneously provide a profile concerning the antimicrobial activity of the eluate against a multitude of test organisms.

2. Prior Art

Absorbency values from UV/VIS spectrophotometer analyses have been obtained for many years. Continuous recording of absorbency values by a monitor connected to the spectrophotometer has been practiced for a long time. The continuous analysis of a flowing stream has been a part of the technology for decades.

In the past the practice has been to cut out a portion of a continuous stream flowing through a UV/VIS spectrophotometer wherein an absorbency value of apparent significance has been indicated. That spot sample would then be analyzed against a series of test organisms by bioautograph processes.

Such a procedure is cumbersome and requires constant monitoring to determine when to take the sample contemporaneously with the spectrophotometer indication of a significant absorbency value.

Accordingly it is an object of this invention to provide an apparatus adapted to continuously record the UV/VIS spectrophotometer absorbency values of a continuous stream of chromatography eluate containing antimicrobial constituents and further adapted to divide such an eluate stream into a plurality of eluate streams for coordination with the bioautograph test results of the latter streams against test organisms, and to accomplish such coordination without the need for continuous visual monitoring of the absorbency values of the eluate stream.

Another object of this invention is to provide a method for using such an apparatus in conjunction with bioautograph tests for effectively and rapidly determining the antimicrobial activity of all of an eluate stream containing antimicrobial constituents.

SUMMARY

Now it has been discovered that by recording the UV/VIS spectrophotometric absorbency values of an eluate stream from a chromatographic column, said eluate stream having antimicrobial constituents therein, and splitting said stream of eluate into a plurality of smaller streams and further depositing such streams continuously on an absorbent material an apparatus is provided, when combined with bioautograph test results, to coordinate such absorbency values with such test results to provide a profile of the antimicrobial activity of the eluate from the chromatographic column against a wide range of test organisms.

DESCRIPTION OF THE PREFERRED EMBODIMENTS

In the following detailed description of the embodiments of this invention, reference is made to the accompanying drawings.

One embodiment of the instant invention is an apparatus used in a method for coordinating UV/VIS absorbency values of a stream of eluate from a chromatographic column, said eluate having constituents therein with antimicrobial activity against a plurality of test organisms. Such an apparatus is comprised of: (a) A UV/VIS spectrophotometer adapted to continuously monitor the absorbency values of an eluate stream flowing continuously therethrough; (b) A pair of parallel metering valves connected by a conduit with the discharge port of said spectrophotometer; (c) A stream splitter adapted to divide a stream of eluate from said spectrophotometer into a plurality of streams having essentially equal volumes connected by a conduit to the discharge port of the first of the pair of parallel metering valves; (d) A conduit connected at one end to the discharge port of the second of the pair of metering valves and at the other end to a waste disposal; (e) Conduits connected at one end to the stream splitter of (c), each disposed thereon to communicate with the location from which each of the divided streams is discharged therefrom, and at the other end disposed immediately above the drum of (f); (f) a drum adapted to hold affixed thereto a sheet of absorbent material and further adapted to rotate in a plane immediately below the ends of the conduits of (e); and, (g) means to rotate the drum of (f).

Figure 1:
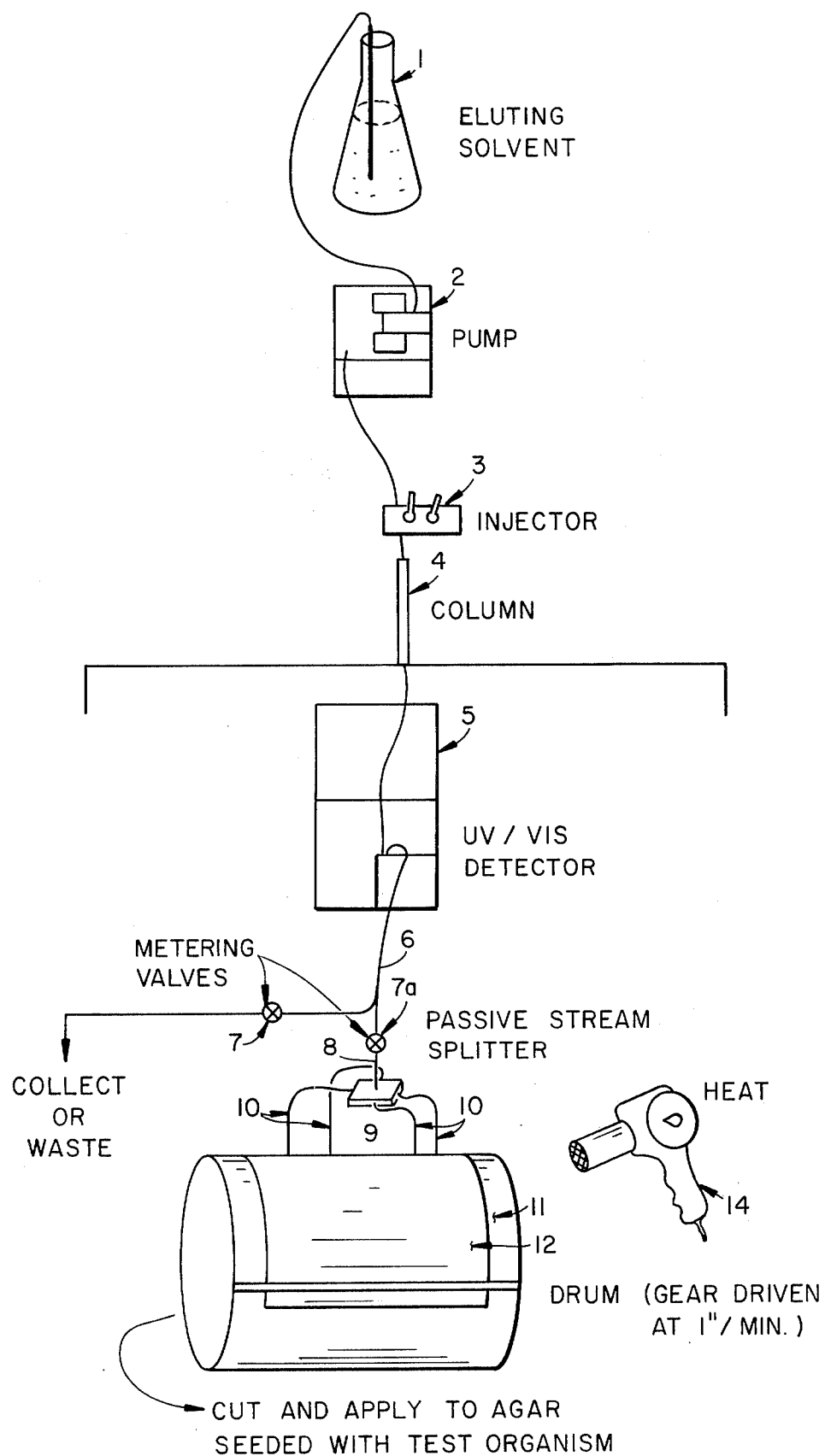
FIG. 1 is a schematic depiction of the series of elements which are combined to constitute the instant invention.

Referring to FIG. 1, there is shown a schematic progression of the elements which are in connected in series to accomplish to objective of this invention. A portion of these elements; namely the eluting solvent 1, the pump 2, the injector 3, and the chromatographic column constitute no part of this invention. They are illustrated only to depict the complete series. The elements which comprise the instant invention are shown as 5 through 12 in FIG. 1, and 13 in FIG. 3. The dryer 14 shown in FIG. 1 is an optional element and consequently is not essential to the instant invention.

The UV/VIS spectrophotometer 5, shown in FIG. 1 is a common instrument, made by a number of companies and well known to those skilled in the art. In this invention the UV/VIS spectrophotometer is adapted to receive, analyze and discharge a continuous stream of a solution. In this invention the solution is preferably an eluate from a chromatographic column, preferably a high pressure column containing an adsorbent from which previously adsorbed material is being eluted. The spectrophotometer is equipped with a monitor which continuously records the absorbency values indicated by the spectrophotometer as the stream of eluate flows therethrough. As is well known to those skilled in the art, a UV/VIS spectrophotometer can be rigged to indicate absorbency values in any number of ranges. Illustratively, the spectrophotometer can be equipped with a detector that detects light at 280 nm. A sample of the eluting solvent can be placed parallel with the flow of the eluate stream and the amount of light absorbed at 280 nm by the constituents in the eluate stream indicated on the continuously recording monitor.

As shown in FIG. 1, the stream of eluate leaving the UV/VIS spectrophotometer is conveyed through conduit 6 to a pair of parallel metering valves 7 and 7a. The pair of metering valves 7 and 7a serve to divert that part of the eluate stream not required for the purpose of providing a plurality of small streams of eluate to a waste, or fraction, collector, and to regulate the pressure of the eluate stream entering the stream splitter 9. The eluate is conveyed through conduit 8 from the first of the two parallel metering valves 7a to stream splitter 9.

Figure 3:
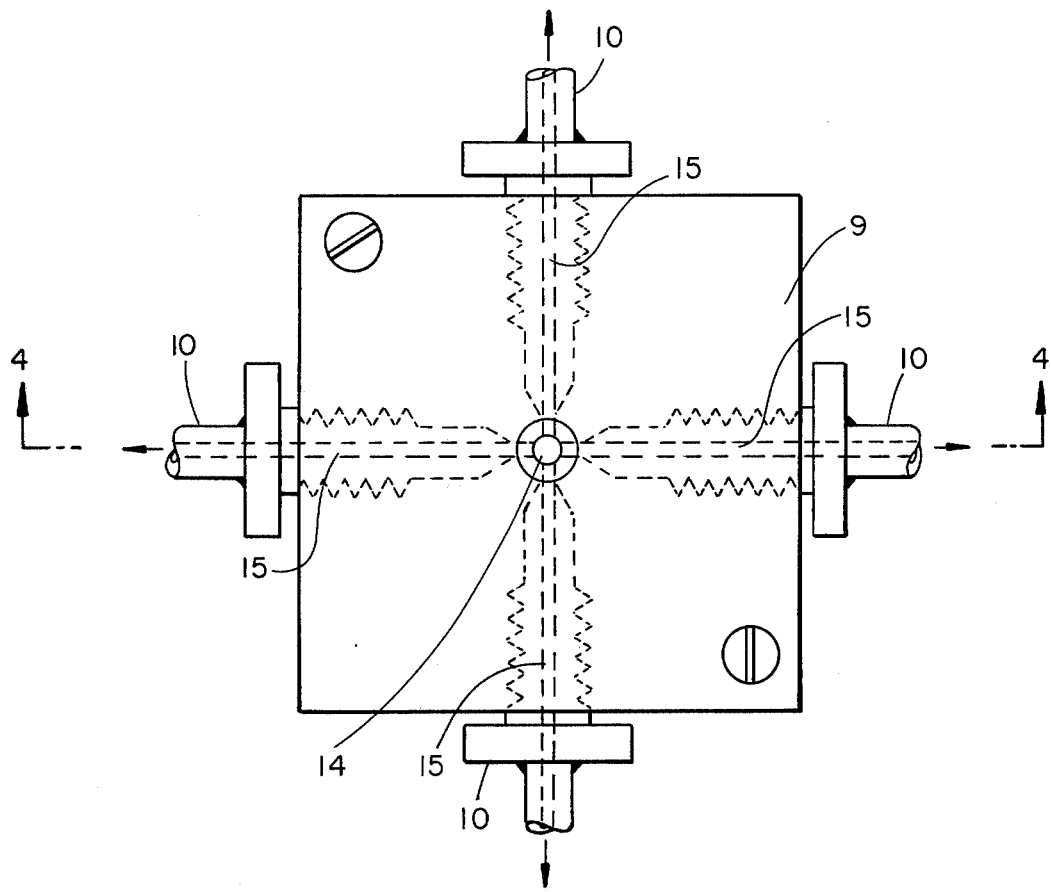
FIG. 3 is a top plan view of the stream splitter showing the internal arrangement by the use of broken lines.
Figure 4:
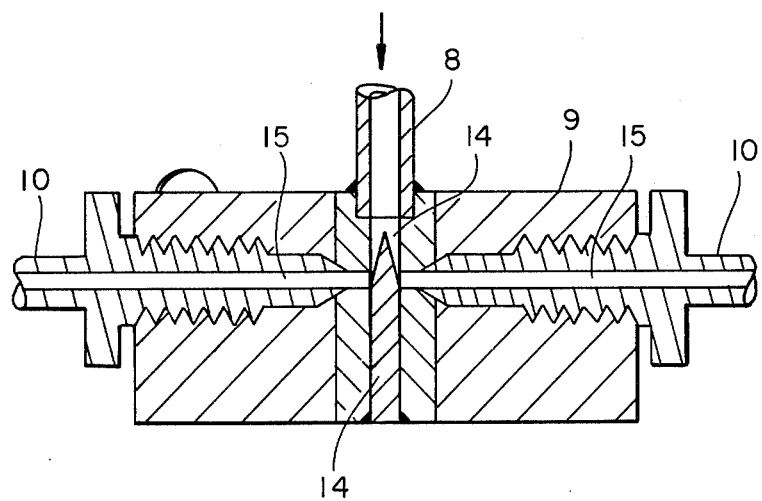
FIG. 4 is a cross-sectional view of the stream splitter of FIG. 3 showing the internal arrangement of the inlet, chamber and metering orifices.

The stream splitter 9 shown in greater detail in FIGS. 3 and 4, is the heart of the instant invention. More about this later.

Four conduits 10 are shown conmmunicating between stream splitter 9 and a position immediately above drum 11. Each of the conduits 10 terminates at a different location immediately above the absorbent material 12 affixed to drum 11. FIG. 1 also shows a dryer 14, which is optional for removing the eluting solvent from the absorbent material element of the instant invention. Not shown in FIG. 1, but depicted in FIG. 3, is the means 13 to rotate drum 11, which is a part of the invention.

Figure 2:
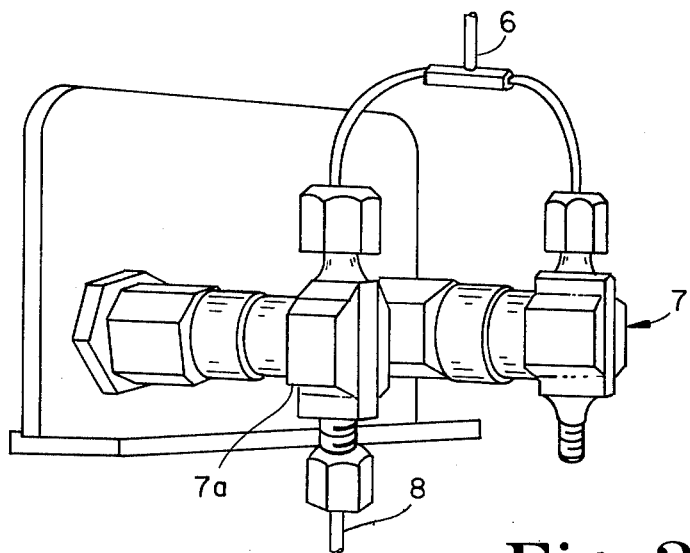
FIG. 2 is a profile rendering of the pair of parallel metering valves which feed the desired amount of eluate into the stream splitter.
Figure 5:
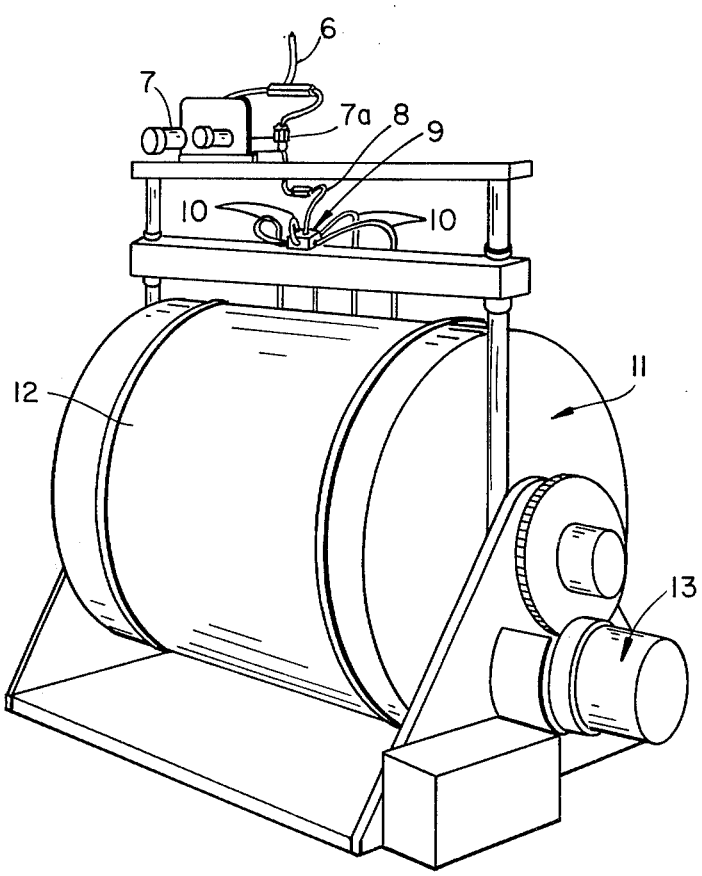
FIG. 5 shows a profile view of the manner the pair of parallel valves of FIG. 2, the stream splitter of FIGS. 3 and 4 and the rotatable drum and means to rotate said drum relate.

The pair of parallel metering valves 7 and 7a are more clearly seen in FIG. 2. The conduit 6 which connects with the discharge from the UV/VIS spectrophotometer is seen to split and connect with the inlet to said metering valves 7 and 7a. The pair of metering valves 7 and 7a can be selected from the group of valves known as gate, globe, and needle. Needle valves are preferred for their adaptability to more precise metering.

Conduit 8 is shown at the outlet from metering valve 7a. The outlet from metering valve 7 can be connected to any convenient waste disposal. The configuration depicted in FIG. 2 is for illustration only. Any installation which places the two metering valves 7 and 7a in a parallel disposition suffices in the spirit of this invention.

The heart of the instant invention is shown in FIGS. 3 and 4. This is the stream splitter. In the FIG. 4 there are four metering orifices 15 communicating between the chamber 14 and the conduit 10. It is important that each of these orifices be of essentially the same inside diameter and length. When this configuration is utilized an essentially equal volume of eluate will flow from chamber 14 through each orifice 15 to conduit 10 when a constant pressure is applied to the eluate in chamber 14. In the illustration, stream splitter 9 is a square block with chamber 14 in the center thereof with conduit 8 communicating with said chamber 14. Each of the four orifices are of equal length and lead to conduits 10 at 90° angles from chamber 14.

In practice, stream splitter 9 could just as well be a rectangle, a triangle, a hexagon, an octagon, or whatever; the requirement being that each orifice be of equivalent diameter and length. And, from the geometric configurations described immediately above, two, three, six or eight orifices of equal length could be employed. In such an arrangement the metering is set by the mechanical arrangement and the volume of flow is altered simultaneously through each by adjusting the pressure in chamber 14. FIG. 3 shows a top view with the internal configuration of the chamber 14 and the orifices 15 depicted with the broken lines. FIG. 4 is a cross-sectional view of stream splitter 9 as illustrated in FIG. 3.

A typical arrangement of the pair of parallel metering valves 7 and 7a, the conduit 6 leading thereto, the conduit 8 leading therefrom to stream splitter 9, the conduits 10 leading from said stream splitter 9 to a position immediately above rotatable drum 11 to which there is affixed a strip of absorbent material 12, and the means 13 to rotate said drum 11.

The absorbent material 12 can be any flexible, porous material such as paper, woven or matted absorbent textile material, and the like. Absorbent paper is preferred for reasons of ready availability in many sizes and grades of absorbency as well as economy.

Most presently used laboratory materials of construction can be employed in the construction of the stream splitter 9 and the conduits 6, 8 and 10. Those skilled in the art know of the chemical resistant of various construction materials to the eluting solvents employed. The preferred needle metering valves are readily available in stainless steel, nylon, polytetrafluoroethylene, and the like. Nylon and polytetrafluoroethylene tubings are also readily available for use as conduits. Other tubings such as polyvinylchloride will serve where no chemical erosion is expected. The stream splitter 9 is preferably made of stainless steel for durability and ease of precision fabrication. However, other material such as nylon or polytetrafluoroethylene can be used successfully.

Another embodiment of the present invention comprises a method for coordinating UV/VIS absorbency values of a stream of eluate from a chromatographic column, said eluate having constituents therein with antimicrobial activity with bioautograph test results against a plurality of test organisms. Such a method is comprised of the following steps: (a) The eluate stream is passed continuously through a UV/VIS spectrophotometer adapted to continuously monitor the absorbency values of said eluate stream. (b) The eluate stream exiting the UV/VIS spectrophotometer is conveyed to a pair of parallel metering valves. (c) The parallel metering valves are adjusted so that a portion of the eluate from the UV/VIS spectrophotometer is directed to a stream splitter and the remaining portion of the such eluate is directed to a waste disposal. (d) The eluate stream flowing through the first of said metering valves is conveyed to a stream splitter. (e) The eluate stream from (d) is split into a plurality of streams of essentially equal volume. (f) Each of the eluate streams from (e) is conveyed to a separate point on a piece of absorbent material affixed to a drum adapted to be rotated. (g) The drum is rotated at a rate that allows each eluate stream contacting said absorbent material to be absorbed in a narrow band as said drum is rotated. (h) The eluting solvent is evaporated from the absorbent material. (i) The absorbent material is divided into strips whereon one of the eluate stream was absorbed. (j) Each of the strips from (i) is contacted with a bioautograph media containing one desired test organism. (k) The bioautograph test media is developed. And, (l) The UV/VIS absorbency values are related and correlated with the reading from the developed bioautograph test media.

The useful method of this invention permits the determination of the antimicrobial activity of a mixture of constituents in a single eluate stream from a chromatographic column simultaneously against a plurality of test organisms. The method is particularly useful in getting a rapid determination of the antimicrobial activity of the constituents of an antibiotic culture against a plurality of test organisms.

For example, a new micoorganism which produces metabolites believed to have antimicrobial activity can be cultured in the manner known to those skilled in the art and the metabolites removed from the culture medium by method known to those skilled in the art. The metabolites can then be absorbed on a suitable chromatographic material such as silica gel, attapulgite, kaolin, bonded phase microparticulates and the like in a chromatographic column, preferrably a high pressure column. Then an eluting solvent can be pumped through an injector into and through such a column and the various constituents absorbed on the chromatographic column will be eluted therefrom as the eluting solvent flows through the column. However, depending upon the strength of the absorbency between the constituents and the absorbent, the various constituents will be eluted at different times as the eluting solvent passes through the chromatographic column. Consequently, the eluate stream will not, generally, contain the same concentration of constituents throughout the eluting process. So by monitoring the absorbency values of the stream of eluate so that at any one wave length, illustratively 280 nm, the degree or percentage of absorbency of light at that wave length in relation to the eluting solvent will be indicated on the recording monitor at the time during the flow when such absorbency takes place.

Then by splitting that stream of eluate into many smaller streams and continuously absorbing such small streams on an absorbent material and developing a bioautograph of each small stream of eluate against a test organism the absorbency values recorded on the UV/VIS spectrophotometer monitor can be related to the point or place on the bioautograph where antimicrobial activity is indicated.

This useful method provides a rapid way to evaluate the potential activity of any constituent of a new microorganism culture. For example, if activity is indicated against only one or two relatively insignificant test organisms a quick and confident decision can be made relative to the potential worth of such a microorganism as a source of new and useful antibiotic material.

Any one of many brands of UV/VIS spectrophotometers can be used in the novel method of this invention. The spectrophotometer must provide for a continuous flow through of a stream containing constituents which will absorb light at one or more of the wave lengths which can be detected by the spectrophotometer. Generally, the instrument will provide for a parallel comparison of the absorbency of the solvent in which the absorbing constituents are solutes. For purposes of illustration in this specification it has been indicated that the detector used would be for 280 nm. Such a wave length is one of the wave lengths for which detectors are available. It is to be understood that the spirit of this invention includes all of the wave lengths in the ultraviolet/visible spectrum. Spectrophotometers are old in the art and in the present invention is combined with other elements which when taken together constitute the invention.

In the useful method described herein the parallel metering valves 7 and 7a serve the purpose of metering into the stream splitter 9 an appropriate amount of the eluate stream coming through conduit 6 to provide for the desired number of small streams at a volume adapted to be absorbed in a narrow band on the absorbent material 12. Additionally, the parallel valves provide a means for disposing of the residual eluate stream from the UV/VIS spectrophotometer which is not needed for coordinating the absorbency value with the bioautograph results against test organisms.

The metering valves 7 and 7a can be adapted for micrometer adjustment to assure the most precise volume of flow. In this method it is important that such valves be chemically resistant to the eluting solvent, and, consequently should be constructed of such material as stainless steel, nylon, polytetrafluoroethylene, and the like.

The method requires also that the conduits 6, 8 and 10 should be chemically resistant to the eluting solvent. Such tubing as nylon, polyvinylchloride, polytetrafluoroethylene, and the like can be employed. Those skilled in the art will recognize the proper material of construction for a particular use.

The stream splitter 9 can be any device by which the eluate stream being conveyed through conduit 8 can be split into a plurality of smaller streams. The mechanical stream splitter described above is preferred because it is capable of reproducibly delivering essentially equal volumes of eluate from each orifice. Other means by which the stream could be split would include a manifold or chamber from which leads were connected to manually, or even automatically, controlled valves. This kind of means for splitting the stream is within the scope of the present method but the mechanical splitter is preferred for the reasons hereinbefore detailed.

In this invention it is contemplated that the streams emanating from the splitter will be conveyed to a position immediately above a rotatable drum on which there is affixed a piece of absorbent material. The method does not require that the ends of such conduits 10 are terminated just above said absorbent material since a more or less natural absorption is preferred and if the ends contact the absorbent material they will act as spreaders. If the ends of conduits 10 are terminated to far above the absorbent material 12 there is a danger of splashing and the obtaining of an uneven distribution.

Rotable drums, such as that contemplated in this invention, to which various materials can be affixed to perform various functions are old in the art. In this invention a piece of absorbent material, such as paper, woven or matted absorbent textiles, and the like, is affixed to the rotable drum to receive the stream of eluate and absorb it in a narrow band. In operation the drum, with the absorbent material affixed thereto is generally rotated at a peripheral speed of 1 inch per minute, and the volume of eluate flowing from conduit 10 onto the absorbent material is adjusted by changing the pressure on chamber 14 of stream splitter 9 to provide the proper amount. Other drum rotation speeds and volumes of eluate discharged onto the absorbent material can be employed. Those skilled in the art will recognize that the faster the drum rotates the greater the volume of eluate required.

Paper is preferred as the absorbent material for reasons hereinbefore discussed.

Generally at the rates hereabove described the eluting solvent will evaporate from the absorbent material shortly after the eluate is deposited thereon. However, if such does not occur a simple electric dryer depicted as 14 in FIG. 1 can be employed to remove the solvent.

Once all of the desired eluate has been deposited on the absorbent material in the desired number of streams and the solvent removed therefrom, the absorbent material is divided into strips each of which contains one stream of eluate.

Previously prepared media containing a test microorganism is contacted by each of the divided absorbent material strips and the media developed by incubating for from 24 to 72 hours depending on the test organism. The media slant should be of sufficient length and width to accommodate the absorbent material strips.

After the media has been developed, the zones of inhibition of growth of the test organism are noted and related to the position on the strip of absorbent material with corresponds to the position of the zone of inhibition. The location on the strip of absorbent material so corresponding is coordinated with the indication on the UV/VIS monitor recording of the absorbency values of the eluate stream at the moment such stream was deposited on the absorbent material.

Those skilled in the art will know that there is a lag time between the time coordinate on the monitor recording and the moment the eluate is deposited on the absorbent material. One visible way to coordinate the lag time with the eluate deposit is to observe the exact moment of the initial deposit and manually record such event on the monitor record. All time lag calculations are then only a matter of simple arithmetic. Other ways to make such coordinations are known to those skilled in the art and can be practiced with equal facility and precision.

The resulting coordination of UV/VIS absorbency values with bioautograph test results provides important information as to the presence or absence of useful antimicrobial activity in the eluate from the chromatographic column.

What is claimed is:

1. An apparatus for coordinating UV/VIS absorbency values of a stream of eluate from a chromatographic column, said eluate having constituents therein with antimicrobial activity, with antimicrobial activity against a plurality of test organisms which comprises:
    (a) a UV/VIS spectrophotometer for continuously monitoring the absorbency values of said eluate stream flowing continuously therethrough;
    (b) a conduit connected at one end to said spectrophotometer and at the other end to a pair of parallel metering valves;
    (c) a conduit connected to the discharge side of the first of the two metering valves and at the other end to a stream splitter, and a conduit connected to the discharge side of the second metering valve and at the other end to a waste disposal;
    (d) a stream splitter connected to the conduit from said first metering valve and which divides the eluate stream from said valve into a plurality of independent eluate streams;
    (e) a plurality of conduits each of which is connected at one end to said stream splitter at an outlet to receive one of the plurality of eluate streams from said stream splitter and the other end of which is open and disposed immediately above the drum of (f);
    (f) a drum having affixed thereto a piece of absorbent material around the circumference of said drum, said drum disposed below the conduits of (e); and
    (g) means to rotate said drum.

2. The apparatus of claim 1 wherein the pair of parallel metering valves are selected from the group consisting of gate, globe and needle valves.

3. The apparatus of claim 1 wherein the stream splitter has an inlet into a chamber from which a plurality of metering orifices of essentially the same cross sectional area and length emanate to convey essentially equal volumes of the eluate flowing into said chamber to an external outlet to which a conduit is connected.

4. A method for coordinating UV/VIS absorbency valves of a stream of eluate from a chromatographic column, said eluate having constituents therein with antimicrobial activity, with bioautograph test results against a plurality of test organisms comprising:
    (a) passing said eluate stream continuously through a UV/VIS spectrophotometer for continuously monitoring the absorbency values of said eluate stream;
    (b) conveying the eluate stream exiting the UV/VIS spectrophotometer to a pair of parallel metering valves;
    (c) adjusting said parallel metering valves so that the eluate stream passing through the first of said valves is directed to a stream splitter and the eluate stream passing through the second of said valves is directed to a waste disposal;
    (d) conveying the stream of eluate from said first metering valve to a stream splitter;
    (e) splitting the stream of eluate from (d) into a plurality of streams of essentially equal volume;
    (f) conveying each of said eluate streams from (e) to a separate point on a piece of absorbent material affixed to a drum adapted to be rotated;
    (g) rotating said drum at a rate that allows each eluate stream to be absorbed in a narrow band on said absorbent material;
    (h) evaporating the solvent from the absorbent material;
    (i) dividing the absorbent material into strips whereon one of the eluate stream was absorbed;
    (j) contacting each of the strips from (i) with a bioautograph media containing one desired test organism;
    (k) incubating the bioautograph media; and
    (l) relating the UV/VIS absorbency values with the test results shown on the incubated bioautograph media.

5. The method of claim 4 wherein the pair of parallel metering valves are adjusted in a manner to feed the portion of the eluate stream flowing from the spectrophotometer to the stream splitter at a pressure that coordinates the volume of eluate flowing from the stream splitter to the absorbent material with the capacity of the absorbent material to absorb the eluate with the rate of rotation of the drum to which the absorbent material is affixed.

6. The method of claim 4 wherein the stream splitter divides the stream of eluate entering thereinto into a plurality of individual streams of essentially equal volume by forcing the eluate under pressure through a plurality of metering orifices of essentially the same cross sectional area and length to an external connection on said stream splitter.

7. The method of claim 4 wherein a tube connected to the discharge from each metering orifice on said stream splitter conveys the eluate to a point immediately above the absorbent material affixed to said drum.

* * * * *